Figure 1:
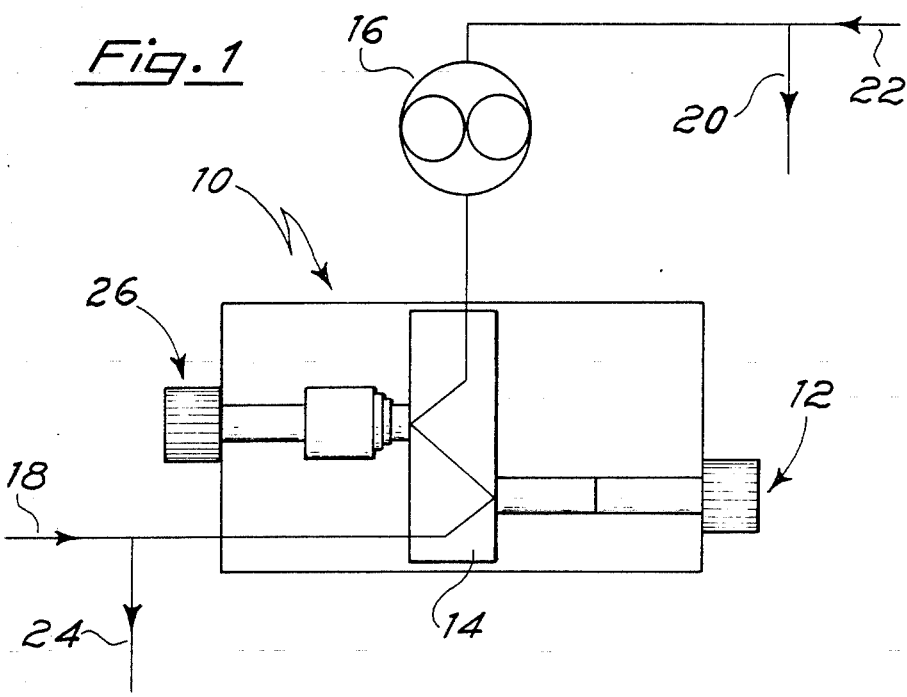

United States Patent [19]

Premoli et al.

[11] Patent Number: 4,618,587
[45] Date of Patent: Oct. 21, 1986

[54] METHOD FOR THE QUANTITATIVE DETERMINATION OF CALCIUM IN BIOLOGICAL FLUIDS THROUGH DIRECT POTENTIOMETRY

[76] Inventors: Pietro Premoli, Via S. Lorenzo 19, Andorno Micca, Vercelli, Italy, 13061; Angelo Manzoni, Via Ugo Foscolo 22, Brugherlo, Milan, Italy, 20047; Claudio Calzi, Via Martiri Oscuri 21, Milan, Italy, 20125

[21] Appl. No.: 703,649

[22] Filed: Feb. 21, 1985

[30] Foreign Application Priority Data

Feb. 28, 1985 [IT] Italy ............................. 19826 A/84

[51] Int. Cl.$^4$ ....................... G01N 27/46; G01N 33/48
[52] U.S. Cl. ............................................. 436/74; 73/1 R;
 204/1 T; 204/409; 436/8; 436/79; 436/16
[58] Field of Search ................ 204/1 A; 436/74, 79, 436/8, 16; 73/1 R

[56] References Cited

U.S. PATENT DOCUMENTS 3,932,233 1/1976 Ruzicka et al. ............... 204/195 M
3,957,607 5/1976 Simon et al. ....................... 204/180 P
4,410,631 10/1983 Czaban et al. ............................ 436/8

OTHER PUBLICATIONS

J. D. R. Thomas, "Ion–Selective Electrode Reviews", vol. 3, p. 192, (1982).
Henry Freiser, "Ion–Selective Electrodes in Analytical Chemistry", vol. I, pp. 272–278, (1978).
Arthur K. Covington, "Ion–Selective Electrode Methodology", vol. II, pp. 55 & 56, (1980).
L. Keil et al., Analyst, 102, 274, (1977).

Primary Examiner—G. L. Kaplan
Attorney, Agent, or Firm—Lowell H. McCarter

[57] ABSTRACT

A method is disclosed for determining calcium ion content of serum which comprises calibrating a potentiometric analytical system with calcium standards having a solution containing both TRIS and BisTRIS at a pH of 7.5. The serum sample is diluted with a silicone oil/water emulsion which may further contain a protein complexing agent such as iron, zinc, cadmium, nickel or copper. Measurement is then carried out on the diluted serum sample.

7 Claims, 2 Drawing Figures

U.S. Patent  Oct. 21, 1986  4,618,587

METHOD FOR THE QUANTITATIVE DETERMINATION OF CALCIUM IN BIOLOGICAL FLUIDS THROUGH DIRECT POTENTIOMETRY

Studying the method for the potentiometric determination of the total calcium in biological fluids forming the matter of the present invention the following documents have been considered:

(a) Patents: U.S. Pat. Nos. 3,957,607, 4/1976, Simon et al. 204/195 M; 3,932,233 1/1976, Ruzicka et al. 204/195 M.

(b) Publications (1) MOORE W. E. "Studies with ion-exchange calcium electrodes in biological fluids; some applications in biomedical research and clinical medicine" in R. A. Durst—Ion selective electrodes. NBS special publications 314 pages 215-285.

(2) SCOTT J. B. and BRADWELL A. R. Identification of the serum binding proteins for iron, zinc, cadmium, nickel and calcium. Clin chem. 29, 629-633 (1983).

(3) D. AMMAN, H. B. JENNY, P. C. MEIER and W. SIMON New ion selective electrodes and their clinical and biological application in Electroanalysis in Hygiene, environmental, clinical and pharmaceutical chemistry. Proceedings of a conference, organized by the electroanalytical group of the Chemical Society of London, held at Chelsea College, University of London, Apr. 17-20, 1979. Edited by W. Franklin Smith. Elsevier Scientific Publishing Company.

The teaching of the above cited prior documents has been duly considered, modified and improved, and in the end we arrived to the present method.

This invention relates above all to a method for the quantitative determination of total calcium content in serum where this ion is present in both free and complex forms (See Moore W. E.).

The measuring system adopted entails the use of a calcium (II) ion selected potentiometric sensing element coupled to a reference electrode (saturated calomel/potassium chloride in this case).

The Calcium (II) ion selective electrode consists of a solid film of plastic material, preferably polyvinylchloride, containing the electroactive material ("neutral carrier" type described by Simon et al.—in U.S. Pat. No. 3,957,607 or of the "ion-exchanger" type described by Ruzicka et al. in U.S. Pat. No. 3,932,233), in an appropriate plasticizer.

A second object of the invention is the automatic determination of total calcium content in serum by diluting the sample in a buffer solution pH 7.5.

The method in accordance with the invention represents a valid alternative to techniques such as atomic absorption spectroscopy or colorimetry and fluorimetry which are widely used in determining total calcium content in serum or other biological fluids.

When this method is employed in conjunction with the particular automatic system chosen, it gives the total calcium concentration in the serum by measuring the electromotive force following the electrochemical system as reported below or other equivalent system: Hg; $Hg_2Cl_2$; sat. KCl//sample/$Ca^{++}$ membrane/$10^{-2}$ $CaCl_2$. AgCl; Ag.

To the present specification of the method according to this invention, for better understanding, and only for example, we annex drawings, in which more precisely:

FIG. 1 is a block diagram of the apparatus which can be used to carry out the method in accordance with the invention.

Figure 2:
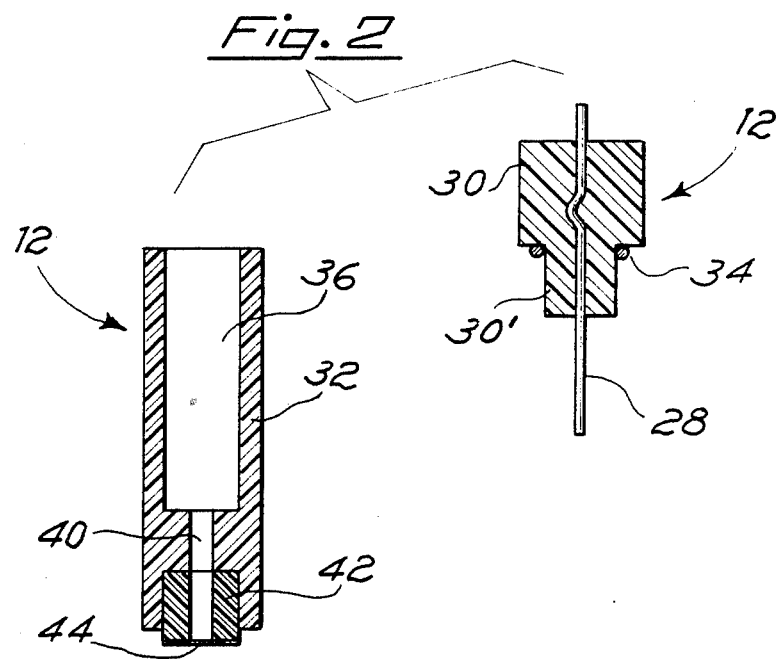

In FIG. 2 it has been shown schematically the calcium ion selective electrode for showing the constructive details of it.

As shown in the drawings:

Measuring electrode 12 and reference electrode 26 are contained within an anodized aluminium block 10 for temperature stability purposes.

The measuring cell or chamber consists of a block of transparent acrylic material 14 incorporating sample flow passages with inlet at 18 and outlet at 20.

All measurements are carried out at ambient temperature.

The sample is aspirated preferably by means of a peristaltic pump 16 with flow rate 1 ml/min.

The electromotive force is measured in the first fifteen seconds, this being the time necessary for stable measurement.

22 denotes the inlet for the reverse flow rinsing fluid and 24 its outlet.

The calcium ion selective electrode, comprises (FIG. 2) a silver wire 28, a body in two sections 30, 32, as well as O-ring 34, membrane 44 and Tygon seal ring 42.

32 denotes a housing 36 containing the filling solution and 30' the narrower diameter section of closing piece 30.

Housing 36 runs into another housing of narrower diameter 40 which besides holding the filling solution, also contains silver wire 28.

All that being stated, the method of the present invention will be considered more in detail.

The sample to be analyzed (serum, plasma, urine, or the standard solution for calibration) is diluted in the ratio 1:20 with a buffer (0.1M) of pH 7.5 at 25° C.

Buffers used at this pH include Tris(hydroxymethyl)aminomethane(Tris) and Tris derivatives.

A silicone oil/water emulsion is added to this buffer in the ratio 1 part emulsion to 9-19 parts buffer.

The purpose of this is to improve electrode performance by almost totally eliminating the memory effect, thereby allowing maximum optimum surface involvement of the calcium ion sensitive membrane.

Moreover, this system differs from the other ones currently available on the market, in that it does not employ acidification of the sample, therefore it guarantees stability and long life of the electrodes. The concentrated emulsion was prepared by homogenizing silicone oil (of type DC 200 Dow Corning of AK 10 Waker) with non ionic surfactants (of type Brij 35 I.C.I. or Antarox Co 530 GAF).

The preferred silicone oil is a dimethyl siloxane polymer that has a density of about 0.8 grams per milliliter, sold by Dow-Corning under the designation "200 Fluid-1 centistoke." Any conventional non-ionic surfactant, as well as the silicone oil, can be selected according to the normal knowledge of the technical expert in the art and are not critical ingredients to the method described and claimed herein.

The calcium is contained in the serum in both ionic form and complexed form with certain proteins (Scott J. B. and Bradwell A. R.). Therefore addition of a protein complexing agent (D. Amman, H. B. Jenny et al.) to the buffer displaces the calcium-protein complexing equilibrium towards the ionic form.

The complexing agent was chosen from metals exhibiting binding affinity towards proteins (Scott J. B. and Bradwell A. R.) such as iron, zinc, cadmium, nickel and copper.

The best experimental results were obtained by adding 0.2 mmols/l zinc to the buffer solution used for dilution.

The considerations arrived at and the results obtained in the experimental phase proved of fundamental importance in the formulation of the system calibration solutions.

Experiments carried out on the automatic system in question showed that by appropriately diluting the serum, plasma and urine in the buffer, the quantity of complexed calcium is constantly kept below 4 to 5% (reference value is determined by atomic absorption spectroscopy).

This percentage of inaccuracy is in the same order of inaccuracy found on electrodes for bivalent ions under normal operating conditions.

At the same time it was found that this difference is independent of protein concentration in the serum within the range 4.5 to 8.5 g/dl.

Hence calibration solutions were formulated as close as possible (as regards calcium content, either ionic or complexed) to the solutions to be measured.

The best results were obtained when using 2,2-Bis-(hydroxymethyl)-2,2', 2''-nitrilotriethanol (BIS-TRIS) in the preparation of standards used for determining suitable calibration curves.

As the "Bis-Tris" exhibits a chelating (or complexing) affinity towards calcium, it corrects the calibration curve without any alteration of the electrode's electrochemical properties.

Furthermore, it was found that addition of "Bis-Tris" between 300 and 400 mg/dl was not critical.

The basic composition of the calibration solutions employed was the same as that of the buffer used for dilution, without, however, the ionic agent ($Zn^{++}$), and with the "Bis-Tris" and calcium chloride.

Lastly, the method in accordance with the invention, also provides, after each calibration or analysis, the automatic rinsing in counterflow direction to that of the normal sampling cycle, using a buffered solution of known calcium composition.

Various experimental tests have been made on the method according to the invention. They make the matter of the following examples.

EXAMPLE 1

The influence of the buffer solution used for dilution was assessed by comparing the results obtained (percentage recovery) with those of a reference analytical technique (Atomic Absorption Spectroscopy A.A.S.).

The buffer solution was prepared by dissolving 2.73 mg $ZnCl_2$ in 100 ml Tris buffer 0.1M and adjusting to required pH with hydrochloric acid.

Calibration was carried out by using solutions of $10^{-3}$ and $3.10^{-3}$M of calcium in Tris buffer 0.1M pH 7.5 containing 3.5 g/l of "Bis-Tris". Dilution ratio was 1:20.

Table (1) sums up the results

TABLE 1

| pH | $Ca^{++}$ (method described)/$Ca^{++}$ A.A.S. in percent |
|---|---|
| 7.0 | 95 |
| 7.2 | 98 |
| 7.5 | 100 |
| 8.0 | 95 |

TABLE 1-continued

| pH | $Ca^{++}$ (method described)/$Ca^{++}$ A.A.S. in percent |
|---|---|
| 8.5 | 80 |

EXAMPLE 2

The effect of protein concentration in the serum was assessed by using test serums from different sources.

Formulation of the Tris buffer pH 7.5 is described in example (1) which also gives the composition of the calibration solutions.

The samples were diluted in the ratio 1:20 and the results compared with those obtained through A.A.S.

Table (2) sums up the results obtained.

TABLE 2

| Test serum | Protein g/dl | $Ca^{++}$ISE/$Ca^{++}$ A.A.S. % |
|---|---|---|
| Monitrol I | 6.7 | 99 |
| Monitrol II | 5.6 | 98 |
| Ortho Abnormal | 4.6 | 100 |
| Roche P | 6.3 | 99 |
| Q Pack I | 4.6 | 100 |
| Seronorm | 6.6 | 99 |
| Pathonorm L | 4.8 | 100 |
| Pathonorm H | 8.4 | 99 |

EXAMPLE 3

The influence of $Zn^{++}$ concentration in the buffer solution used for dilution was assessed by adding a variable quantity from 0.05 to 0.5 mmols/l of $Zn^{++}$ to the uffer described in example (1) which also describes the composition of the calibration standards. Dilution ratio was 1:20.

TABLE 3

| $Zn^{++}$ mmols/l | $Ca^{++}$ (method described)/$Ca^{++}$ A.A.S. % |
|---|---|
| 0.05 | 97 |
| 0.1 | 99 |
| 0.15 | 99 |
| 0.2 | 100 |
| 0.25 | 99 |
| 0.3 | 99 |
| 0.4 | 97 |
| 0.5 | presence of precipitate in the diluting solution |

EXAMPLE 4

Here the influence was assessed of adding a silicone oil/water emulsion to the buffer for improving level of accuracy of the method in accordance with the invention.

The concentrated emulsion was prepared by homogenizing silicon oil—10% (DC 200 Dow Corning or AK 10 Waker) with 1% surfactant (Brij 35 I.C.I. or Antarox Co 530 GAF).

The as-prepared solution was diluted with the buffer described in example (1) in the ratio one part emulsion to 9 parts buffer.

Calibration and dilution were carried out as described in example (1).

Table (4) sums up the results.

TABLE 4

| N° of samples | 50 |
|---|---|
| Linear correlation | y = −0.022 + 1.02 X |

TABLE 4-continued in which:
X = A.A.S.
y = method described (I.S.E.)
Correlation coefficient 0.95

EXAMPLE 5

The influence was assessed of adding the emulsion described in example (4) as rinsing solution (1 part emulsion to 9 parts tris buffer) in order to improve level of accuracy of the method in accordance with the invention.

Table (5) sums up the results.

TABLE 5

| (Within day precision) | |
|---|---|
| N° (serums) | 10 |
| $\bar{x}$ (mmols/l) | 1.95 |
| SD | $8.8 \cdot 10^{-3}$ |
| C.V. (%) | 0.449 |
| N° (serums) | 10 |
| $\bar{x}$ (mmols/l) | 2.73 |
| SD | $1.05 \cdot 10^{-2}$ |
| CV (%) | 0.386 |
| N° (serums) | 10 |
| $\bar{x}$ (mmols/l) | 3.30 |
| SD | $1.5 \cdot 10^{-3}$ |
| CV (%) | 0.4697 |

EXAMPLE 6

The influence was assessed of the amount of Bis-Tris added to the calibration solution in the range 0.3 to 0.4 mg/dl.

Calibration and dilution were carried out as described previously.

Table (6) sums up the results obtained with three different concentrations of Bis-Tris.

Dilution ratio was 1:20 and comparative method was through A.A.S.

TABLE 6

| Test serum | % $Ca^{++}$ Bis-Tris 0.3 mg/dl | according to the method claimed Bis-Tris 0.35 mg/dl | $Ca^{++}$/according to A.A.S. Bis-Tris 0.4 mg/dl |
|---|---|---|---|
| Pathonorm L | 99 | 100 | 100 |
| Pathonorm H | 98 | 99 | 100 |
| Seronorm | 99 | 100 | 101 |
| Roche N | 100 | 100 | 101 |
| Roche P | 99 | 99 | 101 |
| Hyland N | 99 | 100 | 102 |
| Hyland P | 98 | 100 | 101 |
| Monitrol I | 99 | 100 | 101 |
| Ortho Abnormal | 98 | 99 | 100 |

We claim:

1. In a method for the determination of calcium ion content of serum using a potentiometric system the improvement comprising the steps of calibrating the potentiometric system with a first calibrating solution containing about 0.001 molar calcium and a second calibrating solution containing about 0.003 molar calcium, the first and second calibrating solutions also containing about 0.1 molar tris(hydroxymethyl)aminomethane or derivatives thereof having a pH value of about 7.5 at about 25° C. and from about 300 to about 400 milligrams per deciliter of 2.2 Bis-(hydroxymethyl)-2,2',2"-nitrilotriethanol, and diluting a serum sample with a dilution solution containing 0.1 molar tris(hydroxymethyl)aminoethane having a pH value of about 7.5 at about 25° C.

2. The method of claim 1 wherein the dilution solution also contains 1 part emulsion per 9 to 19 parts dilution solution wherein the emulsion is a silicone oil/water emulsion.

3. The method of claim 1 wherein the dilution solution also contains a complexing agent selected from the group consisting of iron, zinc, cadmium, nickel and copper.

4. The method of claim 3 wherein the complexing agent is zinc and is present between about 0.05 to about 0.4 mmols/l.

5. The method of claim 4 containing $Zn^{++}$ as $ZnCl_2$ in concentration ranging from about 0.3 mmols per liter.

6. The method of claim 1 wherein the dilution solution contains a silicone oil/water emulsion prepared by homogenizing said oil from 10 to 20% with non-ionic surfactant from 1 to 5% in water.

7. The method of claim 1 where the calibrating solutions and serum sample are diluted with the dilution solution wherein the dilution ratio ranges between about 1:10 to about 1:50.

* * * * *